United States Patent [19]

Kessler

[11] 4,012,951
[45] Mar. 22, 1977

[54] ACOUSTIC EXAMINATION METHODS AND APPARATUS

[76] Inventor: Lawrence W. Kessler, 418 Warren Road, Glenview, Ill. 60025

[22] Filed: Mar. 8, 1976

[21] Appl. No.: 664,650

[52] U.S. Cl. .............................. 73/67.6; 73/67.5 H; 340/5 H; 340/5 MP
[51] Int. Cl.² ...................................... G01N 29/04
[58] Field of Search .......... 73/67.5 R, 67.5 H, 67.6, 73/71.3; 340/5 MP, 5 H

[56] References Cited

UNITED STATES PATENTS

| | | | |
|---|---|---|---|
| 3,585,848 | 6/1971 | Korpel | 73/67.5 H |
| 3,790,281 | 2/1974 | Kessler et al. | 73/67.5 H X |
| 3,805,225 | 4/1974 | Bossaert et al. | 340/5 H |

Primary Examiner—Richard C. Queisser
Assistant Examiner—John P. Beauchamp
Attorney, Agent, or Firm—Kinzer, Plyer, Dorn & McEachran

[57] ABSTRACT

An acoustic microscope system in which the insonification frequency $f_s$ is continuously modulated, at a rate asynchronous relative to the optical scanning frequencies, to minimize acoustic speckle; the filter means employed to develop a video signal from the scanning beam has its center frequency continuously varied to track the insonification frequency changes. The filter means employs a constant-frequency IF stage, utilizing an IF mixer that subtracts $f_s$ from the initial scanning information but adds a fixed carrier to allow for subsequent effective filtering. A combined deflector and demodulating light shield structure provides for improved alignment of the system optics. For optically opaque specimens, a polished surface of the specimen is used as the acoustic-optic interface, with no coverslip required and both optical and acoustical images derived from a single scanning beam. Shear-mode insonification is employed for improved resolution and to examine special properties of some materials.

29 Claims, 5 Drawing Figures

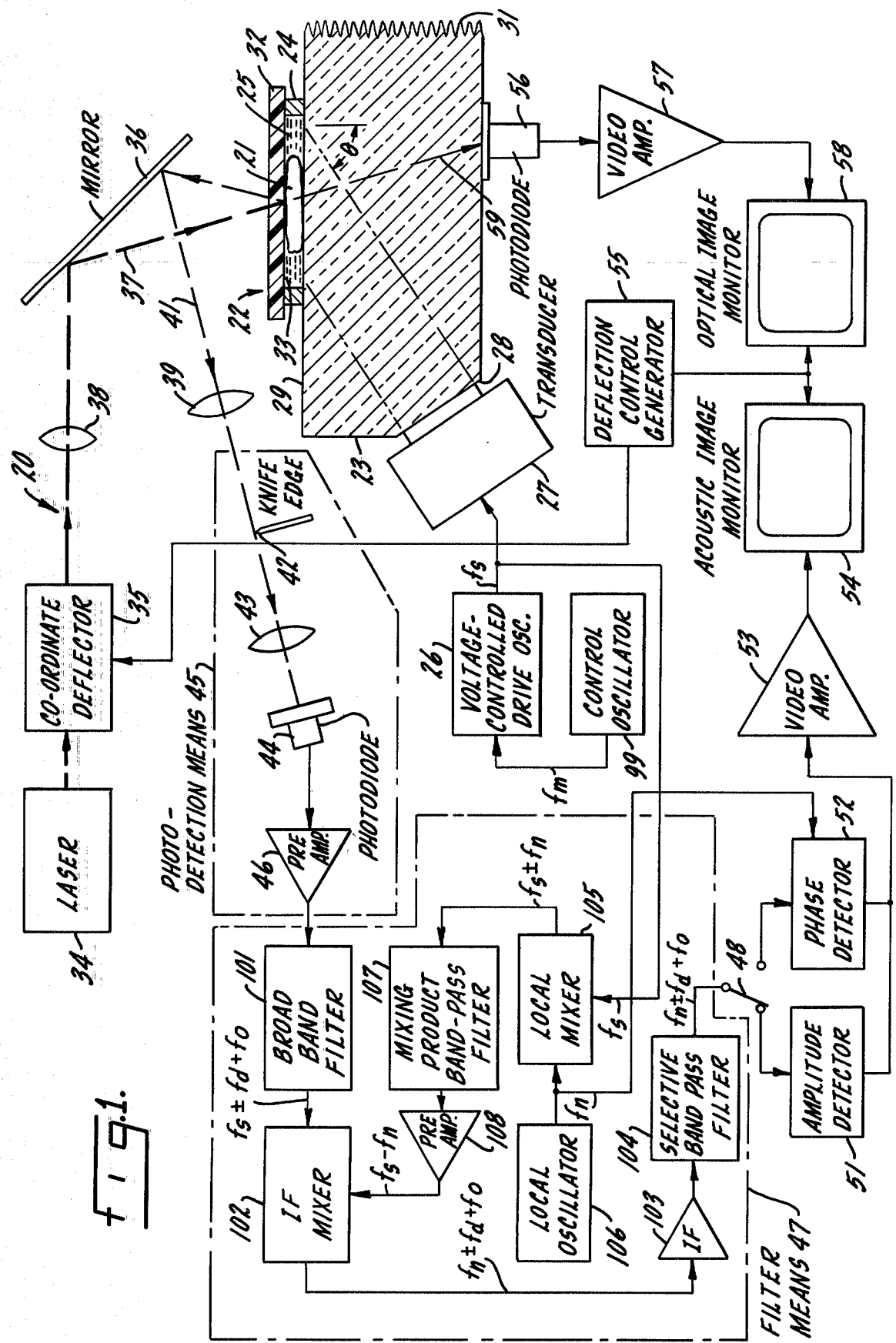

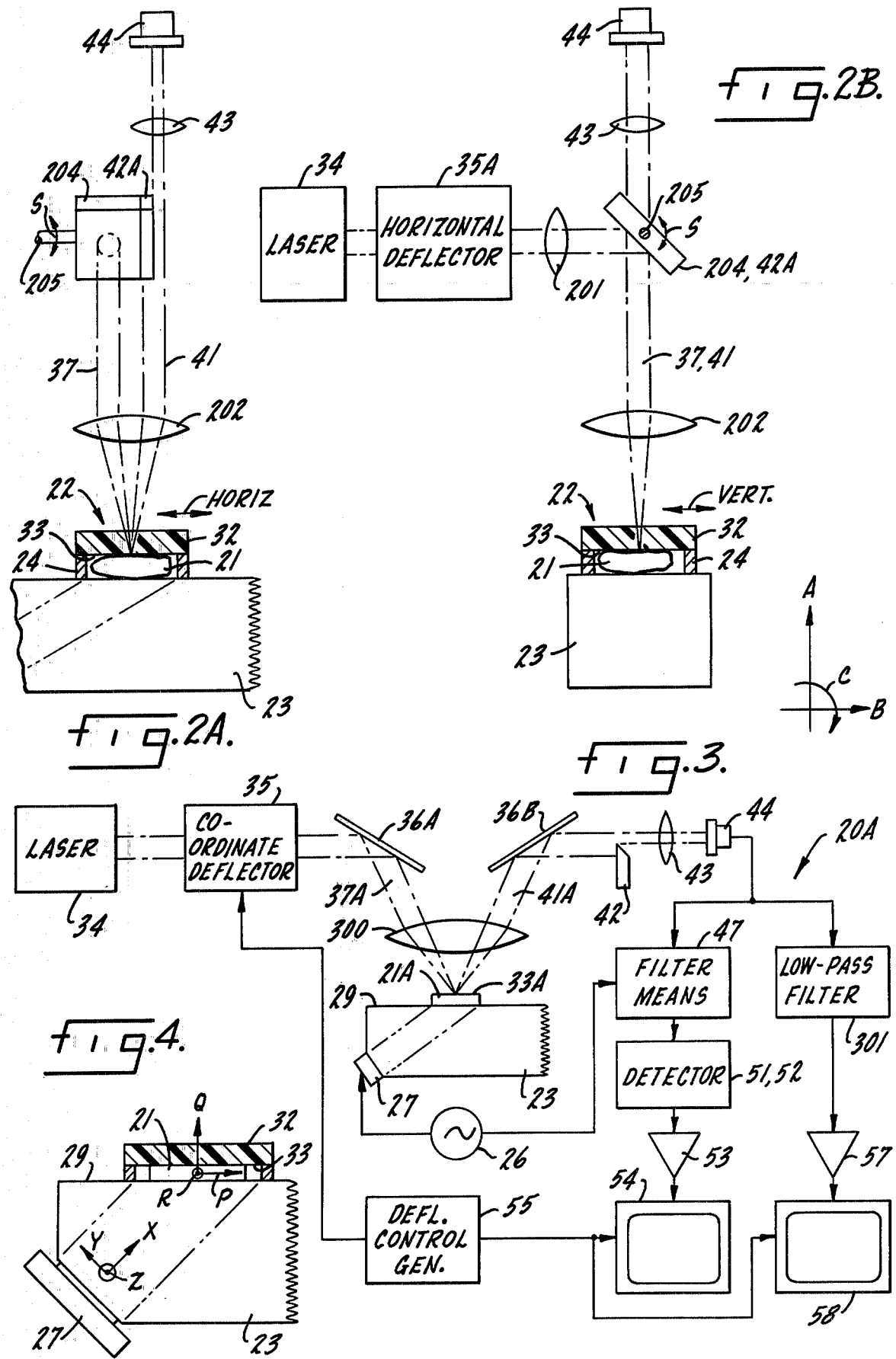

ACOUSTIC EXAMINATION METHODS AND APPARATUS

BACKGROUND OF THE INVENTION

Acoustic microscopes and other like acoustic inspection systems are utilized to determine physical characteristics of objects that cannot be ascertained by more conventional optical examination techniques; for example, see U.S. Pat. Nos. 3,585,848 and 3,790,281. Thus, acoustic microscopy can reveal details of mechanical structure, such as bonding, polymerization, elasticity, density, and viscosity that are not directly revealed by inspection of the electronic structure that is indirectly observed through optical inspection. In addition, an acoustic microscope, even in instances in which it shows the same structural detail as an optical microscope, frequently affords a major quantitative difference in its display as compared with an optical image. For example, the optical reflection from a water-air interface may amount to no more than two percent whereas the acoustic reflection is virtually total. Further, correlated acoustical and optical images of a given specimen may provide total information substantially exceeding that available from one of the images alone.

One problem encountered in acoustic microscopy is "acoustic speckle", comprising spurious image patterns created by interference between acoustic signals which pass through a specimen and arrive at a detection plane with a coherent time invariant phase relationship. This spurious detail may mask pertinent portions of the structure of the specimen and may afford a substantially erroneous image of it.

Another problem encountered in acoustic microscopes, and particularly in the microscope constructions described and illustrated in the aforementioned U.S. patents, pertains to the maintenance of effective alignment of the optical scanning portion of the microscope. Thus, it is frequently difficult to maintain the required precise alignment between the incident high intensity scanning beam that is used to develop acoustic information and the reflected scanning beam carrying that information, relative to the elements of the optical system that demodulate the reflected beam and convert it to usable electrical signals. These problems are accentuated by the frequent necessity for re-positioning the portion of the mechanism that supports the object under examination in order to compensate for differences in thickness and other characteristics of the objects examined.

One of the most practical and effective acoustic microscopes heretofore known, that of U.S. Patent No. 3,790,281, utilizes light from the scanning beam that passes through the object under examination as a basis for development of an optical image that can be compared with the acoustic image. That system, however, does not afford a comparable or effective optical comparison image for specimens that are optically opaque. Nevertheless, for such optical specimens it is still desirable to have a direct optical image of the object under examination for comparison purposes in order to avoid erroneous conclusions that might be drawn from the acoustic image alone.

SUMMARY OF THE INVENTION

It is an object of the present invention, therefore, to provide a new and improved acoustic imaging system and method, suitable for use in acoustic and acoustic-optical microscopy, that effectively and inherently minimizes the difficulties of previously known systems as described above.

A particular object of the invention is to provide a new and improved method and apparatus, for use in an acoustic imaging system such as an acoustical microscope, that effectively minimizes or eliminates acoustic speckle. A feature of the invention, in achieving this object, comprises continuous modulation of the insonification frequency at a rate which is asynchronous relative to the optical scanning frequencies, coupled with the use of filter means, employed to develop a video signal from the scanning beam, that has its center or base frequency continuously varied to track the modulation of the insonification frequency.

Another object of the invention is to provide a new and improved optical system for an acoustic microscope in which a part of the optical demodulation apparatus is physically combined with a scanning beam deflector in a fixed relationship that does not require modification to accommodate the inspection of objects of varying sizes and other characteristics. In support of this object, deflection of the incident scanning beam is effected by a mirror that is mounted upon a common support with a light shield or knife edge utilized to demodulate the reflected beam, so that these critical elements of the optical system remain in precise accurate alignment with each other at all times.

A further object of the invention is to provide a new and improved comparative inspection system for correlated acoustical and optical examination of an object that is optically opaque. A related feature of the invention is the provision of low pass and high pass filter means, coupled to a photodetector that receives a reflected beam from a polished surface of an opaque system; the filters segregate the information in the electrical signal developed by the photodetector to afford both an acoustic image signal representative of internal structure of the object and an optical image signal representative of surface optical appearance of the object.

Another object of the invention is to provide a new and improved acoustic imaging system, suitable for use in microscopy, which affords improved resolution. In support of this object, the invention provides for the utilization of insonification waves polarized in the shear mode rather than in the compressional mode. For an-isotropic materials, the shear mode insonification further reveals details of the object under examination that would not otherwise be visible in the acoustic image.

BRIEF DESCRIPTION OF THE DRAWINGS

FIG. 1 is a block diagram of a comparative inspection system for correlated acoustic and optical examination of a specimen, constructed in accordance with one embodiment of the present invention;

FIGS. 2A and 2B are simplified side and end views, respectively, illustrating a modification of the optical scanning apparatus for the system of FIG. 1;

FIG. 3 is a block diagram, similar to FIG. 1, of another embodiment of the present invention; and FIG. 4 illustrates polarization relationships that may be utilized in the operation of the systems of FIGS. 1-3 and other similar systems.

DESCRIPTION OF THE PREFERRED EMBODIMENTS

The acoustical and acoustical-optical inspection systems of the present invention utilize a distortion that occurs at an elastically deformable interface surface, having finite acoustic impedance, when the interface is subject to an incident acoustic wave. Thus, when an elastically deformable interface surface intercepts an incident plane wave $I_s$ having a velocity V, at an angle of incidence $\theta$, the acoustic wave $I_s$ produces a ripple pattern on that surface. The ripple pattern is dynamic, with fluctuations occurring at the acoustic frequency. The phase of the ripple pattern or displacement wave propagates at a velocity $V'$, with $$V' = V/\sin \theta.$$

In one form of acoustical microscope, as described in "An Acoustic Microscope Operating at 100 Mhz", Nature, Vol. 232, page 110 (1971), the interface is formed by a plastic resin faceplate or coverslip disposed on top of a sound cell filled with a fluid sonic propagation medium, frequently water. The acoustic impedance of a resin faceplate can be reasonably matched with water; moreover, because the resin is quite lossy, acoustically, the acoustic energy transmitted to the coverslip can be effectively propagated into space, thereby avoiding resonance effects. The ripple pattern on the coverslip is made optically reflective by a metallic coating applied to the interface surface. The interface can then be illuminated with a focused laser beam, producing a reflected beam angularly modulated by the changes in slope of the reflective interface surface caused by the propagation of the ripple pattern across that surface. The reflected beam can then be imaged onto a knife edge for conversion of the angular modulation into intensity modulation. The intensity modulated beam is intercepted by a suitable photodetection device, which develops an electrical signal coherent with the local sound pressure at the interface.

An object to be subjected to acoustical examination is placed just under the coverslip, and casts a sharply defined ripple pattern on the interface that is characteristic of the acoustic properties of the object. For inspection of an object of substantial thickness, or in other instances in which the plane of interest in the object cannot be located immediately adjacent the coverslip, the phase of the signal developed from the reflected beam can be analyzed to produce an acoustic hologram of the object; the hologram can subsequently be reconstructed optically in accordance with known techniques. For specific coverslip materials, resolution characteristics, and preferred angles of incidence, reference may be made to U.S. Pat. No. 3,790,281.

FIG. 1 illustrates a comparative inspection system 20, constructed in accordance with one embodiment of the present invention, for correlated acoustical and optical examination of an object such as a specimen 21. System 20 comprises a sound cell 22, including a base member 23 formed from a material exhibiting extremely low acoustical absorption loss, such as fused quartz. Specimen 21 is supported on member 23 within a chamber formed by a spacer 24 and is immersed in a fluid sonic propagation medium 25, which may be water.

System 20 includes insonification means for insonifying object 21 with high frequency acoustic energy. The insonification means is a high-frequency sonic drive oscillator 26 having its output coupled to an electro-acoustic transducer 27 mounted on an angled surface 28 of base member 23 in sound cell 22. The acoustic plane waves developed in base member 23 by transducer 27 impinge upon object 21 at an incidence angle $\theta$. The end 31 of base member 23 opposite surface 28 can be of irregular configuration, affording a sound scattering boundary, or is terminated with an acoustically lossy material.

Inspection system 20 further comprises boundary means defining an elastically deformable, partially light-reflective interface surface that is coupled to object 21 by the fluid sonic propagation medium 25. This boundary means comprises a faceplate or coverslip 32 formed of a resin material such as polymethylmethacrylate or polycarbonate. For this particular embodiment of the system, coverslip 32 must be at least partially transparent. The interface surface 33 of coverslip 32 is in engagement with the fluid propagation medium 25; surface 33 is coated with a thin vacuum-deposited metal coating or is otherwise treated to be partially light-reflective.

Optical scanning means are incorporated in system 20 to develop a high-energy light beam of small diameter and to deflect that beam across interface surface 33 in a regular scanning pattern. The optical scanning means comprises a laser 34 which generates a collimated light beam of very small diameter. The beam from laser 34 passes through a coordinate deflector 35 and impinges upon a mirror 36 that directs the beam along a path 37 through coverslip 32 and onto interface surface 33 in the region immediately above object 21. Deflector 35 may comprise a pair of acoustical-optical light deflector cells of the kind described in "A Television Display Using acoustical Deflection and Modulation of Coherent Light", Applied Optics, Volume 5 page 1667 (1966).

Miror 36 intercepts a first fraction of beam 37 that is reflected from interface surface 33 and directs the reflected fraction of the beam along a path 41. A lens 39, positioned on path 41, forms a 1:1 telescope with a lens 38 interposed in the path of the original beam between deflector 35 and mirror 36. The telescope formed by lenses 38 and 39 images the exit pupil of deflector 35 onto a knife edge 42 positioned to block one-half of the reflected portion 41 of the light beam.

Knife edge 42 is incorporated in a photodetection means 45 for receiving the reflected fraction 41 of the light beam and developing an initial electrical signal representative of an acoustical image of object 21. Photodetection means 45 further comprises a lens 43 and a photodiode 44 that is positioned to interrupt the reflected beam 41 after it has passed knife edge 42. Photodiode 44 is electrically connected to the input of an amplifier 46. The output of amplifier 46 is coupled to the input of a filter means 47.

The output of filter means 47 is connected to a single-pole double-throw switch 48 having two output terminals which are connected, respectively, to the input of an amplitude detector 51 and to the input of a phase detector 52. Phase detector 52 has a second input used for phase synchronization. The output of detectors 51 and 52 are connected, through a video amplifier 53, to a first image reproducer 54, comprising a television monitor, oscilloscope, or other appropriate image-reproducing device. Image reproducer 54, sometimes referred to herein as the acoustic image monitor, also receives coordinate deflection control signals from a deflection signal generator 55. The deflection control generator 55 is also coupled to the light beam coordinate deflector 35 to maintain synchronism between deflection of the light beam and of the image reproducing electron beam in the image monitor.

A part of the incident light beam 37 passes through the semi-reflective interface surface 33 and through base member 23. This transmitted portion 59 of the light beam impinges upon a photodiode 56 that is electrically coupled, through a video amplifier 57, to a second image reproducer 58 essentially similar to image reproducer 54. A deflection control input for image reproducer 58, sometimes referred to as the optical image monitor, is derived from deflection control generator 55 to maintain monitor 58 in synchronism with the operation of monitor 54 and light beam deflector 35.

In operation of system 20, the basic function of the sound cell 22 is to couple acoustic energy to specimen 21, at the desired insonification angle $\theta$, while mechanically supporting the specimen in close coupled proximity to the interface surface 33 of coverslip 32. The high acoustic velocity in the quartz support member 23 (6000 meters/second), compared to the acoustic velocity in the fluid propagation medium 25 (1500 meters/second for water) causes a substantial refraction at the interface between the quartz and the water at surface 29. In cell 22, therefore, the sonic waves from transducer 27 are refracted from the solid into the fluid at a relatively narrow angle, in this instance about 10°. The transmitted sound intensity is about 10 db below that of the incident acoustic beam; the remaining sound is scattered and absorbed within the fused quartz block, support member 23.

Laser 34 develops a phase-coherent high intensity light beam of small diameter which scans specimen 21 in a regular scanning pattern controlled by the deflection control generator 55 and optical deflector 35. A first fraction 41 of the incident beam 37 is reflected from the ripple pattern on the interface surface 33 and impinges upon knife edge 42. The telescope arrangement comprising lenses 38 and 39 maintains the position of the reflected fraction 41 of the light beam, impinging upon knife edge 42, essentially independent of the instantaneous scanning angle. Instead, the light beam position depends only upon the surface distortion produced at interface 33, constituting a ripple pattern characteristic of the acoustic properties of specimen 21.

As the reflected fraction 41 of the light beam changes its position slightly with respect to knife edge 42, in accordance with the acoustical pattern of object 21, the overall intensity of the portion of the beam that reaches photodiode 44 changes. Thus, the electrical signal developed by photodiode 44, which is coherent with the local sound pressure, is amplified, filtered and detected, and is applied to the acoustic image monitor 54, through circuits 46, 47, 51 and 53. A synchronized visual image is developed, on monitor 54, since the deflection control for monitor 54 is derived from the same source 55 that controls the optical deflector 35.

The response of the acoustical microscope portion of system 20, as described immediately above, can be modified optically or by electronic filtering. Electronic modification is possible because the laser probe, scanning the moving ripple pattern upon interface 33, creates a Doppler shift in the signal output, from the sound frequency $f_s$, in accordance with the equation:

$$f_d = V_s/L \sin \theta$$

where $V_s$ is the linear velocity of the scanning light beam 37 across the interface surface 33 and $L/\sin \theta$ is the wavelength of the ripple pattern on the interface surface; $f_d$ is the amount of the Doppler shift. From the equation it is seen that spatial frequencies are translated into temporal frequency changes which can be processed electronically. Electronic filtering is especially important in restricting the angular response to one side of normal incidence, eliminating phase reversals which otherwise may severely distort the acoustical image and produce false image detail.

The sensitivity of the acoustical microscope incorporated in system 20 is governed by several parameters, such as laser power, observation time, detector efficiency, choice of face plate material, and others. For an acoustic frequency $f_s$ of 100 MHz, using a frame time in acoustical monitor 54 of 1/30 second, sensitivities of approximately $10^{-3}$ watts per square centimeter have been obtained. In this system, operating at 100 MHz, resolution of 1.3 wavelengths of sound have been effected, corresponding to a resolution of twenty microns with a sound wavelength of fifteen microns in water. Higher resolutions can be obtained at higher frequencies; thus, at a sonic frequency of one GHz, a resolution of two microns can be expected.

The optical microscope incorporated in system 20 utilizes the transmitted fraction 59 of the original laser beam 37 that passes through object 21. Optical resolution is determined primarily by the diameter of the light beam. The optical image reproduced on monitor 58 and the acoustic image reproduced on monitor 54 are inherently correlated with each other. Because the optical and acoustic images are reproduced simultaneously from different fractions of the same incident light beam, it is a relatively simple matter to adjust the two image monitors to minimize distortion differences and to assure equality in the magnification ratios of the acoustical and optical images, so that substantially exact registry is possible.

To develop an acoustical hologram of specimen 21, switch 48 is actuated from the position shown in FIG. 3 to the alternate position in which the output of filter means 47 is applied to phase detector 52 instead of amplitude detector 51. This results in the generation of a series of lines of equal phase contour in the image developed on acoustic monitor 54. The resultant hologram can be reconstructed, using known optical techniques, to afford better visualization of the out-of-focus portions of specimen 21.

System 20 (FIG. 1) allows direct, side-by-side comparison of two simultaneously generated, directly correlated visual representations of the acoustical and optical images of the object under examination, specimen 21. The two images can be compared directly by the user of the system, the detail in one image aiding in interpretation of detail pertaining to the same portion of the specimen that appears in the other image. On the other hand, in a given application, it may be desirable to superimpose the two images on each other, directly, without the necessity of taking photographs for subsequent processing. Simultaneous imaging on both an acoustical basis and an optical basis is illustrated and described in U.S. Pat. No. 3,790,281.

As thus far described, the combination acoustical-optical microscope system 20 corresponds to the system described in connection with FIG. 3 of U.S. Pat. No. 3,790,281. In utilization of that system with a single fixed insonification frequency $f_s$, however, the acoustic images developed by monitor 54 may include spurious detail due to constructive and destructive interference. This interference arises between signals which pass through specimen 21 and reach the detection plane, interface surface 33, with a coherent and time invariant phase relationship. The spurious detail, called "acoustic speckle", may be of greater contrast than detail representing the structure of specimen 21 and may mask the image of the structure of the specimen. Acoustic speckle is effectively and inherently minimized, in system 20, by the particular constructions adopted for the insonification means comprising oscillator 26 and transducer 27, and for the filter means 47.

In system 20, the insonification drive oscillator 26 is a voltage-controlled oscillator. A free-running control oscillator 99 is incorporated in the insonification means, supplying to oscillator 26 a control voltage that varies at a fixed frequency $f_m$. Frequency $f_m$ must be asynchronous with respect to the frequencies of the horizontal and vertical deflection signals developed by the deflection control generator 55. That is, the control signal frequency $f_m$ should not be an integral multiple or integral sub-multiple of either of the scanning frequencies. This asynchronous relationship should be maintained so that each time a new frame is initiated in the image on monitor 54, the acoustic frequency composition will be different from that of the preceding frame.

Conceptually, by utilizing phase or frequency modulation of the insonification frequency $f_s$, as in the described arrangement for drive oscillator 26 and control oscillator 99, with the frequency or phase of the insonification signal being continuously swept or scanned over a given range, acoustic speckle is effectively eliminated. However, this modification, by itself, is not adequate to afford satisfactory system operation. The initial electrical signal developed by photodiode 44 and supplied to filter means 47 by preamplifier 46 has a frequency spectrum which is centered at the acoustic frequency $f_s$, and has sidebands which correspond to structural details of the specimen 21 and the angle of insonification. As described above, the sideband signals are related to the angle of the sound emerging from specimen 21 and their frequency is determined by the Doppler shift equation set forth above. If insonification occurs normal to interface surface 33, instead of at an angle at surface 29, then unscattered sound strikes interface surface 33 at an angle of 0°. Scattered sound is symmetrical as a function of the angle $\theta$, producing symmetrical side bands at $f_s \pm f_d$.

The bandwidth of filter means 47 must be tailored to accept all desired sideband frequencies from specimen 21 while rejecting undesired sidebands. If the overall effective pass band of filter means 47 is too great, the image developed on monitor 54 suffers a substantial degradation in signal-to-noise ratio. If the overall pass band of filter means 47 is too narrow, resolution in the image reproduced by monitor 54 is reduced as the result of lack of frequency response fidelity. Because the center frequency of filter means 47 must be tailored to the insonification frequency $f_s$, the filter means 47 must "track" changes of $f_s$ by application of the control signal $f_m$ to the voltage controlled drive oscillator 26, without appreciable change in the filter bandwidth. That is, precise tracking of filter means 47 with changes in the insonification frequency $f_s$ is of utmost importance; otherwise, for at least some acoustic frequencies, undesired side bands, including phase reversals which distort the acoustical image and cause the appearance of false detail, will pass through filter means 47 to monitor 54.

As illustrated in FIG. 1, filter means 47 comprises a broad band filter 101 connecting the output of preamplifier 46 to one input of an intermediate-frequency mixer 102. The output of the IF mixer 102 is connected, through an IF amplifier 103 and a selective bandpass filter 104, to switch 48.

Filter means 47 further comprises a mixer 105 to which a constant frequency signal of frequency $f_n$ is supplied from a local oscillator 106 that is also coupled to detector 52. A second input to mixer 105 is a signal at the insonification frequency $f_s$, derived from oscillator 26. The output of mixer 105 is connected, through a band pass filter 107 and an amplifier 108, to a second input to IF mixer 102.

Filter means 47, in the construction disclosed in FIG. 1, incorporates filter modulation means that continuously varies the effective center frequency of the filter means in synchronism with the modulation of the insonification frequency $f_s$. This is accomplished by use of an IF frequency which is maintained constant independently of changes in the acoustic frequency $f_s$.

Mixer 105 receives two inputs, the fixed frequency signal of constant frequency $f_n$ from oscillator 106 and the insonification signal of varying frequency $f_s$ from oscillator 26. The output of mixer 105, accordingly, has a frequency $f_s \pm f_n$. Filter 107 eliminates the upper side band from the output of mixer 105, affording an input to mixer 102, through amplifier 108, having a frequency $f_s - f_n$.

The broad band filter 101 is utilized only to eliminate frequencies which are well outside the information range required for the acoustic image. The output signal from filter 101, which includes all of the essential information plus undesired side bands, has a frequency composition of $f_s \pm f_d + f_o$. That is, the information signal supplied to mixer 102 is centered about the insonification frequency $f_s$ except for an offset constant $f_o$ that is caused by the angular incident insonification.

Due to the action of the knife edge 42, however, the lower side bands of the initial information signal (i.e., frequencies below $f_s$) have a phase inversion of 180° compared with the upper side bands (i.e., frequencies above $f_s$) and must be filtered out before the signal is supplied to either of the detectors 51 and 52. Desired sidebands comprise $f_o \pm f_d$ with an algebraic sum exceeding zero. Mixer 102 shifts the initial signal frequency spectrum in accordance with the local signal $f_s - f_n$, developing an IF signal having a frequency spectrum of $f_n \pm f_d + f_o$. It is readily apparent that the IF signal is independent of changes in the insonification signal frequency $f_s$, due to modulation of the local oscillator signal $f_n$ with the insonification signal frequency $f_s$ in mixer 105. Because the IF frequency is independent of variations in the insonification frequency, the selective band pass filter 104 may be constructed with the requisite precision to allow effective elimination of the undesired lower side band signals, affording an output constituting an image signal having a frequency composition of $f_n \pm f_d + f_o \geq f_n$. It is this image signal that is detected in one of the two detectors 51 and 52 and utilized to drive the acoustic image monitor 54.

At an insonification frequency $f_s$ of approximately 100 MHz, and with an information bandwidth for the acoustic image of about 3 MHz, assuming normal television scanning rates for monitor 54, a rejection of approximately 40 db is required for signals which lie outside the desired information band by 1 MHz or more. If the acoustic frequency $f_s$ is varied (modulated) over a range of 10 MHz, due to the action of control oscillator 99, construction of a conventional bandpass filter with a center frequency varying over that range, while still maintaining the required rejection, is not practical. The illustrated construction for filter means 47, utilizing a constant IF frequency derived from a tracking local oscillator circuit (oscillator 106 and mixer 105), is both practical and highly satisfactory in operational results. The problem becomes even more acute if a wider frequency range is used for the insonification frequency $f_s$ as, for example, by sweeping the insonification frequency $f_s$ over a 30 MHz range. Even with this scope of modulation of the insonification frequency, the fixed IF filter means 47 is capable of maintaining close tracking, with effective elimination of the undesired phase-reversal side bands.

For system 20, the particular modulation frequency selected for control oscillator 99 is not critical except that it must be maintained asynchronous relative to the scanning frequencies as described above. Selection of the control frequency $f_m$ may be made on an empirical basis to afford the most acceptable visual effect in the image reproduced on monitor 54, since the control oscillator frequency does produce some pattern in the acoustic image. In one practical system employing conventional television scanning frequencies, a control frequency $f_m$ of approximately 7 KHz has been found satisfactory.

The frequency selected for local oscillator 106 is also relatively uncritical. In one practical system, utilizing an insonification frequency centered at 100 MHz, a local oscillator frequency $f_n$ of 30 MHz has been employed.

FIGS. 2A and 2B illustrate a modified construction for the scanning and photodetection elements of the acoustic imaging apparatus of system 20 (FIG. 1) that affords substantial advantages as regards alignment of the apparatus for a variety of different specimens and different operating conditions. As shown in FIG. 2, the laser or other high energy light source 34 may be aligned with a single deflector 35A. Device 35A, here designated as a horizontal deflector, may comprise a cell of the kind identified above in relation to the coordinate deflector 35 of FIG. 1. From deflector 35A, the light beam passes through a lens 201 to impinge upon a mirror 204 mounted on a shaft 205. Shaft 205 is rotated by a suitable motor (not shown) as indicated by the arrows S. A galvanometer movement can be utilized as the drive motor for shaft 205.

The light beam 37 reflected from mirror 204 passes through a lens 202 to impinge upon the interface surface 33 between coverslip 32 and specimen 21. The reflected light beam 41 passes back through lens 202 to impinge upon a light absorbing shield 42A, serving as a knife edge to perform the same function as described above in connection with member 42 of FIG. 1. The portion of light beam 41 that passes shield 42A (FIG. 2A) extends through the lens 43 to impinge upon the photodiode 44.

In the configuration illustrated in FIG. 2, lens 201 images the exit pupil of horizontal deflector 35A onto mirror 204. The rotational movement of mirror 204 causes the incident light beam 37 to sweep across the interface surface 33 in a "vertical" direction, from left to right in FIG. 2B. The deflection of the incident beam 37 effected by deflector 35A is in a "horizontal" direction, from left to right in FIG. 2A. Lens 202 focuses the incident beam on the plane of interface surface 33. The reflected beam 41 is directed back through the same lens 202, following which approximately 50% of the reflected beam is intercepted by the knife edge or light shield 42A, which is attached to the mirror 204. Lens 202 is positioned so that the exit pupils of both horizontal and vertical deflectors are coincident and are imaged onto the knife edge 42A; thus, the knife edge is sensitive only to the acoustic modulation impressed upon the reflected laser beam 41. That is, the reflected beam 41, reaching knife edge 42A, is position-modulated by the acoustic signal from the interface surface 33 of coverslip 32. Accordingly, the amount of light which bypasses shield 42A depends upon the instantaneous position of the beam as modulated in response to acoustic waves passing through specimen 21. Lens 43 collects the portion of the reflected beam that passes the knife edge and focuses it upon photodiode 44 to develop an initial electrical signal proportional to light beam intensity, as in the previously described system.

In FIG. 2, the vertical deflector mirror 204 is structurally combined with light shield 42A. This considerably simplifies the precision alignment that is necessary to make the system practically operable as an acoustical microscope. Furthermore, the necessity for maintaining alignment between two separate optical tracks, as in the system of FIG. 1, is eliminated.

Typically, each time a new sample is placed upon the stage afforded by the upper surface 29 of base 23, the position of coverslip 32 and interface 33 is slightly altered, frequently destroying the critical position alignment of the reflected light beam 41 with respect to shield 42A, lens 43, and photodiode 44. With the construction shown in FIG. 2, base member 23 can be conveniently mounted in a positioning mechanism allowing adjustment horizontally and vertically, and also providing for tilting of the base member, as indicated by arrows A, B, and C. This makes it possible to compensate for any displacement of interface surface 33, permitting accurate alignment of the interface with respect to the optical scanning system with no change in the optical apparatus. That is, the operator can exercise complete control over optical alignment merely by adjustment of the staging surface 29; the balance of the optical system can be sealed in permanent alignment. Inasmuch as the positioning mechanism for base member 23 may be of any desired construction, no positioning mechanism has been shown in the drawings.

The acoustical-optical inspection system 20 of FIG. 1 provides for simultaneous development of acoustic and optical images of a specimen on the basis of transmission of both forms of energy through the specimen. Acoustic microscopy is also useful, however, for determining the microstructural characteristics of metals, glasses, crystals, ceramics, and other materials which may be optically opaque and for which an optical through-transmission image cannot be obtained. FIG. 3 illustrates a method and apparatus for inspecting the internal structure of optically polished specimens by means of acoustic microscopy, in combination with generation of a surface optical image that may be employed for comparison purposes.

Much of the system 20A illustrated in FIG. 3 is a repetition of the system illustrated in FIG. 1. Thus, system 20A includes a stage or base member 23 with a transducer 27 mounted thereon and energized from an acoustic signal generator 26. A laser 34 or other high-energy light source develops an intense light beam that is directed to impinge upon a mirror 36A through a coordinate deflector apparatus 35. The reflected scanning beam 37A passes through a lens 300 to impinge upon a sample 21A mounted on the stage surface 29 of base member 23. The reflected beam 41A is directed by another mirror 36B to impinge upon a knife edge or shield 42, with approximately 50% of the beam passing the knife edge through the lens 43 to impinge upon the photodiode 44.

As in the previously described system, the initial electrical signal developed by photodiode 44 is filtered by filter means 47, detected by one of the detectors 51 or 52, and applied as a video signal to acoustic monitor 54. The output of photodetector 44 is also applied to a low pass filter 301 to develop a second image signal that is supplied to the optical monitor 58. As before, a deflection control generator 55 supplies synchronized deflection signals to the optical deflector 35 and to the monitors 54 and 58.

System 20A (FIG. 3) does not utilize a coverslip 32 as in the system of FIG. 1. Instead, the surface 33A of specimen 21A that faces outwardly of base member 23 functions as the interface surface for the system. For effective operation, specimen surface 33A should be optically polished, in the same manner as normally followed in preparing for a metalographic examination.

Thus, in operation of system 20A the polished surface 33A takes the place of the coverslip surface 33 in the previously described embodiment, impressing the acoustic modulation representative of the internal structure of specimen 21A directly on the reflected laser beam 41A. In addition to the modulation of the reflected light beam by the acoustically induced surface changes at interface surface 33A, differences in the optical reflectivity of surface 33A will of course also affect the amount of light that is reflected and that is directed to impinge upon photodiode 44. Thus, the reflected laser beam 41A contains two modulation components, a first component representative of information derived from acoustic energy transmitted through specimen 21A and a second modulation component representative of the visual characteristics of the specimen surface 33A. Although these two modulation components constitute signals that are separated in frequency, the optical signal information modulates the acoustic signal information. Accordingly, acoustic monitor 54 displays an image that is the product of the acoustic properties and the optical surface properties of the specimen examined.

The initial information signal derived by photo diode 44 is processed, as before, in filter means 47 and detector 51 (or 52), and supplied as an image signal to acoustic monitor 54. The optical information in the initial signal developed by diode 44 is at the low frequency end of the spectrum. Consequently, it is separated by low pass filter 301 and supplied as a separate image signal, through amplifier 57, to optical monitor 58. Simultaneous viewing of the acoustical-optical image on monitor 54 and the optical image on monitor 58 affords the observer a basis for comparison, avoiding erroneous conclusions that might otherwise be drawn from the acoustic image alone. Furthermore, visual landmarks on surface 33A of specimen 20A can be directly identified during examination, facilitating experimental practice by circumventing any necessity for removing the specimen from system 20A for examination under an optical microscope for comparative purposes.

In the foregoing discussion of systems 20 and 20A, FIGS. 1 and 3, it has been implicitly assumed that transducer 27 produces ultrasonic compressional waves in base 23, constituting waves in which particle motion is parallel to the direction of wave propagation. Acoustical wave having quite different characteristics can also be developed, however, using known transducer structures. In particular, transducers utilizing lithium niobate or Y-cut quartz vibration elements are known to produce two varieties of transverse or so-called shear mode acoustical waves. In these shear mode ultrasonic waves, the particle motion is perpendicular to the direction of wave propagation. Depending upon the polarization, particle motion will be in the plane of incidence or perpendicular to the plane of incidence of the propagation vector. The plane of incidence is defined by incident and reflected waves at an interface.

FIG. 4 illustrates this polarization phenomenon, as applicable to the apparatus of any of FIGS. 1 through 3. As shown therein, there are two pertinent sets of coordinate axes XYZ and PQR. Transducer 27 may produce shear mode acoustic energy with propagation in the X direction and particle motion polarized in the Y direction. For this arrangement, it is clear that when the acoustic wave reaches the boundary surface 29, there will be a component of particle motion along the Q axis. Accordingly, surface ripples will be produced which are detectable by the scanning laser beam in the same manner as described above for the detection of compressional waves. An advantage to the utilization of shear mode acoustical excitation is that the wavelength is approximately 50% shorter than for a compressional wave of the same frequency. Accordingly, resolution in the acoustical image is improved with shear mode insonification as compared with insonification in the compressional mode.

In the examination of solid materials using compressional mode insonification of the specimen, the acutal image resolution observed in the acoustical image may exceed that which could be anticipated from the wavelength of the acoustical energy. This phenomenon is presented when a mode conversion occurs at a structural interface. That is, the scattered energy from an interface may consist of both compressional wave and shear wave components, even though insonification is of only one type. In many cases, however, the predominant component of the scattered energy will be of the same type as the incident insonfication wave. By utilizing shear mode insonification with polarization in the plane of incidence, the attainable resolution in solids can be materially enhanced in comparison with the resolution achieved otherwise.

A variety of different materials exhibit anisotropic properties. Anisotropy can occur naturally or can be induced by internal stress or other means. Anisotropic materials may cause conversion between compressional and shear modes, but more importantly may cause a change of polarization of the incident acoustic energy.

Referring to FIG. 4, transducer 27 can be oriented to produce shear waves with propagation along the X axis but with particle motion along the Z axis, perpendicular to the plane of the drawing. When a wave of this kind reaches boundary 29, the interface with sample 21, the particle motion is along the R axis with no component in either of the P and Q directions. Mode conversion to a compressional wave will not occur, assuming neither base 23 nor specimen 21 has anisotropic properties. Under these circumstances, there will be no interface displacement which can be picked up by the scanning laser beam.

However, if an anisotropic specimen is placed on the stage surface 29 and insonified with shear mode energy, as described, those components of the scattered waves which produce particle motion in the direction of axis Q produce ripples or perturbations at the interface and will be detected. Thus, with this modification the acoustical microscope discriminates changes in polarization of the acoustical waves caused by passage through the specimen examined. Accordingly, an acoustic image is developed that affords a display of microstructural components which cause polarization rotation of the incident shear mode insonification. With this application, certain material properties which go undetected by optical examination or by conventional acoustical examination can be effectively revealed.

It will be recognized that the various features of the invention can be employed in various combinations. For example, the optical reflection system of FIG. 3 can utilize the deflection apparatus of FIGS. 2A and 2B, instead of a coordinate deflector with fixed mirrors. The polarization modifications of FIG. 4 are readily applicable to the systems of all preceding figures.

I claim:

1. In an acoustic imaging system for developing a visual image representative of the acoustic properties of an object, of the kind comprising:
   an elastically deformable and at least partially light-reflective surface coupled to the object;
   insonification means for insonifying the object with acoustic waves of predetermined frequency $f_s$ to develop a ripple pattern at the interface surface which is characteristic of the acoustic properties of the object;
   scanning means for scanning a high-energy small-diameter light beam across the interface surface;
   photodetection means for detecting the portion of the light beam reflected from the interface surface to develop an initial electrical signal;
   filter means for filtering the initial electrical signal to eliminate sidebands having undesired phase reversals and develop an image signal;
   and imaging means utilizing the image signal to develop a visual image representative of the acoustic properties of the object;
   the improvement comprising:
   sonic modulating means, included in the insonification means, for continuously modulating the insonification frequency $f_s$ at a rate which is asynchronous relative to any scanning frequency employed in the scanning means;
   and filter modulation means, included in the filter means and coupled to the insonification means, for continuously varying the effective center frequency of the filter means in synchronism with the modulation of the insonification frequency $f_s$; thereby minimizing acoustic speckle effects in the visual image.

2. An acoustic imaging system according to claim 1, in which the insonification means comprises a variable-frequency drive oscillator having an output frequency $f_s$ that varies in response to a control signal applied to the drive oscillator, and the sonic modulating means comprises a control oscillator supplying a control signal to the drive oscillator.

3. An acoustic imaging system according to claim 1, in which the filter modulation means comprises:
   a local oscillator for generating a local IF carrier signal of frequency $f_n$;
   local mixer means, coupled to the local oscillator and to the insonification means, for developing an IF modulation signal having a frequency of $f_s \pm f_n$;
   and an IF mixer, coupled to the photodetection means and the local mixer means, for developing an IF signal of constant center frequency $f_n$ independent of variations in the insonification frequency $f_s$.

4. An acoustic imaging system according to claim 3 in which the local mixer means further comprises a band-pass filter limiting the IF modulation signal applied to the IF mixer to one of the two frequencies $f_s + f_n$ or $f_s - f_n$.

5. An acoustic imaging system according to claim 4, in which the insonfication means comprises a variable-frequency drive oscillator having an output frequency $f_s$ that varies in response to a control signal applied to the drive oscillator, and the sonic modulating means comprises a control oscillator supplying a control signal to the drive oscillator.

6. An acoustic imaging system according to claim 1, in which the scanning means comprises:
   a light source for developing a high-energy light beam of small diameter;
   and deflection means for deflecting the light beam across the interface surface in a predetermined scanning pattern;
   and in which the photodetection means comprises:
   a photosensitive device positioned to receive the portion of the light beam reflected from the interface surface;
   and a light shield between the interface and the photosensitive device for intercepting a predetermined fraction of the reflected light beam;
   the light shield and the deflection means being affixed to a common support to maintain alignment between the incident and reflected light beam such that the fraction of the reflected beam intercepted by the light shield remains constant except for the effect of the ripple pattern at the interface surface.

7. An acoustic imaging system according to claim 6 in which the deflection means comprises first and second coordinate deflector devices disposed in series along the path of the incident light beam, and in which the second deflector device is affixed to a common support with the light shield.

8. An acoustic imaging system according to claim 7 in which the second deflector device comprises a rotating mirror.

9. An acoustic imaging system according to claim 1 in which the insonification means includes a transducer which generates acoustic waves, in which the direction of particle motion is approximately perpendicular to the direction of propagation, so that the object is insonified in the shear mode.

10. An acoustic imaging system according to claim 9, in which the transducer generates acoustic waves in which the direction of particle motion is approximately parallel to the plane of the interface surface, so that the visual image is primarily representative of anisotropic structural features of the object.

11. In a method of acoustic imaging comprising the basic steps of:
  A. scanning a high-energy small-diameter light beam across an elastically deformable and at least partially light-reflective interface surface that is coupled to an object to be examined;
  B. insonifying the object with acoustic waves of predetermined frequency to develop a ripple pattern at the interface surface which is characteristic of the acoustic properties of the object;
  C. detecting the portion of the light beam reflected from the interface surface to develop an initial electrical signal;
  D. filtering the initial electrical signal to eliminate sidebands having undesired phase reversals and develop an acoustic image signal;
  E. and utilizing the acoustic image signal to develop a visual image representative of the acoustic properties of the object; the improvement comprising:
  F. continuously modulating the insonification frequency of step B at a predetermined rate which is asynchronous relative to any scanning frequency employed in step A;
  G. and continuously varying the effective center frequency of the filter means employed in step D, in synchronism with the frequency modulation of step F; thereby minimizing acoustic speckle effects in the visual image of step D.

12. The method of acoustic imaging according to claim 11, including the additional steps of:
  H. filtering the initial electrical signal to derive an optical image signal comprising the low-frequency components of the initial electrical signal;
  I. and utilizing the optical image signal to develop a second visual image representative of the external optical properties of the object.

13. The method of acoustic imaging according to claim 12, including the additional step of optically polishing the surface of the object that is to be scanned, prior to imaging, and utilizing the polished surface of the object as the interface surface.

14. The method of acoustic imaging according to claim 11 in which the insonification of step B is effected with shear mode acoustic waves in which the direction of particle movement is approximately perpendicular to the direction of wave propagation.

15. The method of acoustic imaging according to claim 14, in which the direction of particle motion is approximately parallel to the plane of the interface surface, so that the visual image is primarily representative of anisotropic structural features of the object.

16. An acoustic imaging system for developing a visual image representative of the acoustic properties of an object, comprising:
  an elastically deformable and at least partially light-reflective surface coupled to the object;
  insonification means for insonifying the object with acoustic waves of predetermined frequency $f_s$ to develop a ripple pattern at the interface surface which is characteristic of the acoustic properties of the object;
  a light source for generating a high-energy small diameter light beam;
  deflection means for deflecting the light beam across the interface surface in a predetermined scanning pattern;
  a photosensitive device positioned to receive the portion of the light beam reflected from the interface surface to develop an electrical signal representative thereof;
  a light shield between the interface and the photosensitive device for intercepting a predetermined fraction of the reflected light beam;
  the light shield and the deflection means being affixed to a common support to maintain alignment between the incident and reflected beams such that the fraction of the reflected beam intercepted by the light shield remains constant;
  and imaging means utilizing the electrical signal to develop a visual image representative of the acoustic properties of the object.

17. An acoustic imaging system according to claim 16 in which the deflection means comprises first and second coordinate deflector devices disposed in series along the path of the incident light beam, and in which the second deflector device is affixed to a common support with the light shield.

18. An acoustic imaging system according to claim 17 in which the second deflector device comprises a rotating mirror.

19. A comparative imaging system for correlated acoustical and optical examination of an object provided with an optically reflective surface, comprising:
  insonification means for insonifying the object with acoustic energy at a predetermined frequency;
  a light source for developing a high-energy light beam of small diameter;
  deflection means for deflecting the light beam across the optically reflective surface of the object in a predetermined scanning pattern;
  photodetection means for receiving the reflected beam from the reflective surface and developing an initial electrical signal representative of both optical and acoustical characteristics of the object;
  high band pass filter means, coupled to the output of the photodetection means, for developing an acoustic image signal repesentative of the internal structure of the object;
  low-pass filter means, coupled to the output of the photodetection means, for developing an optical image signal representative of the external optical appearance of the object;
  and imaging means utilizing the image signals to generate correlated visual images of the internal acoustical and surface optical images of the object.

20. A comparative acoustical-optical imaging system according to claim 19, in which the photodetection means comprises:
  a photosensitive device positioned to receive the portion of the light beam reflected from the reflective surface of the object;
  and a light shield between the reflective surface of the object and the photosensitive device, for intercepting a predetermined fraction of the reflected light beam;
  the light shield and the deflection means being affixed to a common support to maintain alignment between the incident and reflected light beams such that the fraction of the reflected beam intercepted by the light shield remains constant.

21. A comparative acoustical-optical imaging system according to claim 20 in which the deflection means comprises first and second coordinate deflector devices disposed in series along the path of the incident light beam, and in which the second deflector device is affixed to a common support with the light shield.

22. A comparative acoustical-optical imaging system according to claim 21 in which the second deflector device comprises a rotating mirror.

23. A comparative acoustical-optical imaging system according to claim 19 in which the insonification means includes a transducer which generates acoustic waves, in which the direction of particle motion is approximately perpendicular to the direction of propagation, so that the object is insonified in the shear mode.

24. A comparative acoustical-optical imaging system according to claim 23, in which the transducer generates acoustic waves in which the direction of particle motion is approximately parallel to the plane of the interface surface, so that the visual image is primarily representative of anisotropic structural features of the object.

25. A comparative acoustical-optical imaging system, according to claim 19, and further comprising:
sonic modulating means, included in the insonification means, for continuously modulating the insonification frequency $f_s$ at a rate which is asynchronous relative to any scanning frequency employed in the deflection means;
and filter modulation means, included in the high band pass filter means and coupled to the insonification means, for continuously varying the effective center frequency of the high band pass filter means in synchronism with the modulation of the insonification frequency $f_s$;
thereby minimizing acoustic speckle effects in the acoustical visual image.

26. A comparative acoustical-optical imaging system according to claim 25, in which the insonification means comprises a variable-frequency drive oscillator having an output frequency $f_s$ that varies in response to a control signal applied to the drive oscillator, and the sonic modulating means comprises a control oscillator supplying a control signal to the drive oscillator.

27. A comparative acoustical-optical imaging system according to claim 25, in which the filter modulation means comprises:
a local oscillator for generating a local IF carrier signal of frequency $f_n$;
local mixer means, coupled to the local oscillator and to the insonification means, for developing an IF modulation signal having a frequency of $f_s \pm f_n$;
and an IF mixer, coupled to the photodetection means and the local mixer means, for developing an IF signal of constant center frequency $f_n$ independent of variations in the insonification frequency $f_s$.

28. A method of acoustic imaging comprising the steps of:
A. scanning a high-energy small-diameter light beam across an elastically deformable and at least partially light-reflective interface surface that is coupled to an object to be examined;
B. insonifying the object with shear mode acoustic waves, in which the direction of particle movement is approximately perpendicular to the direction of wave propagation, to develop a ripple pattern at the interface surface which is characteristic of the acoustic properties of the object;
C. detecting the portion of the light beam reflected from the interface surface to develop an initial electrical signal;
D. filtering the initial electrical signal to eliminate sidebands having undesired phase reversals and develop an acoustic image signal;
E. and utilizing the acoustic image signal to develop a visual image representative of the acoustic properties of the object.

29. The method of acoustic imaging according to claim 28, in which the direction of particle motion is approximately parallel to the plane of the interface surface, so that the visual image is primarily representative of anisotropic structural features of the object.

* * * * *